(12) United States Patent
Ullman et al.

(10) Patent No.: US 6,797,481 B1
(45) Date of Patent: Sep. 28, 2004

(54) SIMULTANEOUS SCREENING OF MULTIPLE ANALYTES

(75) Inventors: Edwin F. Ullman, Atherton, CA (US); Marcel Pirio, San Jose, CA (US); Mary C. Ericson, Santa Cruz, CA (US); Daniel B. Wagner, Sunnyvale, CA (US); Dariush Davalian, San Jose, CA (US)

(73) Assignee: Dade Behring Marburg GmbH, Marburg (DE)

( * ) Notice: Subject to any disclaimer, the term of this patent is extended or adjusted under 35 U.S.C. 154(b) by 176 days.

(21) Appl. No.: 09/691,383

(22) Filed: Oct. 17, 2000

(51) Int. Cl.$^7$ ............................................... G01N 33/53
(52) U.S. Cl. ........................... 435/7.1; 435/7.5; 435/7.9; 435/7.91; 435/7.92; 435/7.93; 435/975; 436/164; 436/165; 436/172; 436/518; 436/527; 436/805; 436/811; 436/815; 436/816; 436/817; 436/901
(58) Field of Search ................................. 435/7.5, 7.91, 435/7.92, 7.93, 975, 7.1, 7.9, 7.21, 287.1, 287.2, 288.7, 808; 436/816, 901, 65, 164, 165, 172, 510, 518, 527, 805, 814, 811, 815, 817; 422/55, 82.05, 82.08, 82.11

(56) References Cited

U.S. PATENT DOCUMENTS

| | | |
|---|---|---|
| 3,679,655 A | 7/1972 | Jager |
| 3,935,074 A | 1/1976 | Rubenstein et al. |
| 3,998,943 A | 12/1976 | Ullman |
| 4,160,016 A | 7/1979 | Ullman |
| 4,161,515 A | 7/1979 | Ullman |
| 4,233,401 A | 11/1980 | Yoshida et al. |
| 4,255,329 A | 3/1981 | Ullman |
| 4,256,834 A | 3/1981 | Zuk et al. |
| 4,279,617 A | 7/1981 | Masson et al. |
| 4,281,061 A * | 7/1981 | Zuk et al. ........................ 435/7 |
| 4,506,009 A | 3/1985 | Lenhoff et al. |
| 5,256,575 A | 10/1993 | Hu et al. |
| 5,369,036 A | 11/1994 | Mercolino et al. |
| 5,501,985 A | 3/1996 | Baugher et al. |
| 5,516,636 A | 5/1996 | McCapra |
| 5,567,627 A * | 10/1996 | Lehnen ......................... 436/518 |
| 5,646,001 A * | 7/1997 | Terstappen et al. ......... 435/7.21 |
| 5,661,019 A | 8/1997 | Oh et al. |
| 5,705,338 A | 1/1998 | Piran et al. |
| 5,851,778 A * | 12/1998 | Oh et al. ....................... 435/7.9 |
| 6,251,688 B1 * | 6/2001 | Erb et al. ..................... 436/518 |
| 6,300,082 B1 * | 10/2001 | Erb et al. ..................... 435/7.1 |

FOREIGN PATENT DOCUMENTS

WO     WO 89/03041 A2 *   4/1989      ......... G01N/33/531

OTHER PUBLICATIONS

Zhang et al., "Simulatneous incorporation of two anticancer drugs in DNA". the Journal of Biological Chemistry, 268 (14), May 15, 1993, pp. 10095–10101.*

Maggio et al., "Enzyme–Immunoassay"copyright 1980 by CRC press, Inc. pp. 186–187.*

Wilbur et al., *Biotin Reagents for Antibody Pretargeting. 2. Synthesis and in Vitro Evaluation of Biotin Dimers and Trimers for Cross–Linking of Streptavidin.* Bioconjugate Chem. 1997, 8, 819–832.

* cited by examiner

Primary Examiner—Christopher L. Chin
(74) Attorney, Agent, or Firm—Theodore J. Leitereg

(57) ABSTRACT

Methods, compositions and kits are disclosed. The methods are directed to determining the presence of one or more analytes in a sample suspected of containing any one of a plurality of the analytes. A combination is provided comprising in a medium (i) the sample, (ii) a binding partner for each of the analytes, (iii) for each of the analytes, a first reagent comprising a member of a signal producing system, a ligand and an analyte analog, and (iv) a second reagent comprising a binding partner for the ligand. The binding of the binding partner for the ligand is affected by the presence of an analyte and alters the amount of signal produced by the member of the signal producing system. The signal thus is modulated if one or more of the analytes are present in the sample. The amount of the signal is determined and is related to the presence of one or more of the analytes in the sample. The method may be homogeneous or heterogeneous.

16 Claims, No Drawings

US 6,797,481 B1

SIMULTANEOUS SCREENING OF MULTIPLE ANALYTES

BACKGROUND OF THE INVENTION

1. Field of the Invention

This invention relates to methods, compositions and kits for simultaneously detecting one or more analytes such as drugs in a sample.

The clinical diagnostic field has seen a brad expansion in recent years, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting the presence of these materials in low concentrations is enhanced by the relatively small sample sizes that can be utilized.

Over the last decade, testing for drugs of abuse has become commonplace. This testing is not only for the monitoring of criminal offenders and drug addicts, but employers also use it for the screening of workers. Most multi-analyte assays are heterogeneous, have poor sensitivity and poor dynamic range (2to 100-fold difference in concentration of the analytes is determined) and some require the use of sophisticated instrumentation.

High volume screening for drugs of abuse is currently carried out commercially by conducting a series of individual homogeneous immunoassays (EMIT or FPIA). A cut off level is set for each drug, which is used to establish whether a particular result will be defined as positive or negative. It is necessary for testing laboratories to handle separate reagent sets and carry out separate assays for each of the commonly abused drugs in every sample. Typically, the presence of as many as six drugs must be determined.

Among those homogeneous assays that have been used commercially or are particularly good candidates for drug screening, EMIT®, CEDIA®, FRAT® and SLFIA have the property of having an increase in signal with an increase in drug concentration. However, because of sensitivity problems or problems intrinsic to these methods, assays for low concentration analytes can have relatively high negative signals, sometimes more than 50% of the maximum possible signals. Combined assays, therefore, show a serious loss in sensitivity. Moreover, induced luminescence assays have decreased signals (fluorescence polarization and chemiluminescence, respectively) with increasing drug concentration and are, therefore, poor candidates for a combined drug assay.

Because of the resultant increase in testing, a market has opened up for "quick "Yes or No" tests." These are assays that can test qualitatively for drugs of abuse. Many of the "quick tests" which have been described are designed to be used as "on site" assays, [EZ-SCREEN™ (Editek Inc., Burlington, N.C.), ONTRAK™ (Roche Diagnostics Systems, Inc., Branchburg, N.J.), Triage™ (Biosite Diagnostics, San Diego, Calif.) and ONTRAK TESTCUP-5™ (Roche Diagnostic Systems, Somerville, N.J.)] and a few of them are able to test for more than one drug in a single assay (Triage™ and ONTRAK TESTCUP-5™). In these multi-analyte systems, if any one of the tested drugs is over a threshold limit, a positive result is obtained. Such positive results must then be confirmed by an unrelated method.

2. Brief Description of the Related Art

U.S. Pat. No. 5,661,019 (Oh, et al.) discloses trifunctional conjugates having three chemical moieties attached through a spacer moiety.

U.S. Pat. No. 5,567,627 (Lehnen) describes method and composition for the simultaneous and discrete analysis of multiple analytes.

U.S. Pat. No. 5,340,716 (Ullman, et al.) describes an assay method utilizing photoactivated chemiluminescent labels.

Photoactivatable chemiluminescent matrices are described in U.S. Pat. No. 5,709,994 (Pease, et al.).

SUMMARY OF THE INVENTION

One aspect of the present invention is a method for determining the presence of one or more analytes in a sample suspected of containing any of a plurality of the analytes. A combination is provided comprising in a medium (i) the sample, (ii) a binding partner for each of the analytes, (iii) for each of the analytes, a first reagent comprising a member of a signal producing system, a ligand and an analyte analog, and (iv) a second reagent comprising a binding partner for the ligand. The binding of the second reagent to the ligand alters the amount of signal produced by the member of a signal producing system. The amount of the signal is determined and is related to the presence of one or more of the analytes in the sample. The method may be homogeneous or heterogeneous. In a preferred embodiment, a predetermined increased amount of signal is produced if one or more of the analytes are present in the sample.

Another embodiment of the present invention is a method for determining the presence of one or more analytes in a sample suspected of containing any of a plurality of the analytes. The sample and a binding partner for each of the analytes are combined in a medium. A first reagent is added to the combination for each of the analytes. The first reagent comprises a member of a signal producing system, a ligand and an analyte analog. A second reagent comprising a binding partner for the ligand is added to the combination. The binding of the second reagent to the ligand alters the amount of signal produced by the member of a signal producing system if one or more of the analytes are present in the sample. The medium is examined for the amount of the signal, which is related to the presence of one or more of the analytes in the sample.

Another embodiment of the present invention is a method for simultaneously determining the presence of one or more drugs in a sample suspected of containing any of a plurality of the drugs. The sample and an antibody for each of the drugs are combined. Then, to this combination is added, for each of the drugs, a first reagent comprising a first label, a small molecule and a drug analog. A second reagent is added to the combination. The second reagent comprises a second label and an antibody for the small molecule. The first label and the second label interact in close proximity to produce a predetermined increased amount of signal if one or more of the drugs are present in the sample. The medium is examined for the amount of the signal. An increased amount of signal is related to the presence of one or more of the drugs in the sample above a predetermined cut-off level.

Another embodiment of the present invention is a kit for determining the presence of one or more drugs in a sample suspected of containing any of a plurality of the drugs. The kit comprises in packaged combination (i) an antibody for each of the drugs, (ii) for each of the drugs, a first reagent comprising a first label, a small molecule and a drug analog, and (iii) a second reagent. The second reagent comprises a second label and an antibody for the small molecule. The first label and the second label are capable of interacting in close proximity to modulate a signal if one or more of the drugs are present in the sample.

DESCRIPTION OF THE SPECIFIC EMBODIMENTS

The present invention permits effective screening of samples for the presence of one or more of a plurality of different analytes. In one embodiment the present method is a homogeneous assay that has higher sensitivity, larger dynamic range ($10^3$- to $10^4$-fold difference in analyte concentration), and fewer and more stable reagents than methods known in the art. The present method is simple and reliable.

The analytes to be screened are the compounds or compositions to be detected. The analyte is usually comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as a bacterium or a cell bearing a blood group antigen such as A, B, D, etc., or an HLA antigen or the analyte may be a microorganism, e.g., bacterium, fungus, protozoan, or virus. In certain circumstances the analyte may also be a reference compound, a control compound, a calibrator, and the like.

The monoepitopic ligand analytes will generally be from about 100 to about 2,000 molecular weight, more usually, from about 125 to about 1,000 molecular weight. The analytes include drugs, e.g., drugs of abuse, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoylecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g., phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics, which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g. B12, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin, The next group of drugs is the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormtnes. Other polymeric materials of interest are mucopolysaccharides and polysaccharides.

For receptor analytes, the molecular weights will generally range from 10,000 to $2 \times 10^8$, more usually from 10,000 to $10^8$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as biological tissue, including body fluids, from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The biological tissue includes excised tissue from an organ or other body part of a host and body fluids, for example, urine, blood, plasma, serum, saliva, semen, stool, sputum, cerebral spinal fluid, tears, mucus, and the like.

In accordance with the present method a combination is provided in a medium. The combination comprises (i) the sample, (ii) a binding partner for each of the analytes, (iii) for each of the analytes, a first reagent comprising a member of a signal producing system, a ligand and an analyte analog, and (iv) a second reagent comprising a binding partner for the ligand. In each of the first reagents, the ligand and the analyte analog are closely associated so that the binding of the binding partner for the analyte to the analyte analog blocks binding to a receptor. In this way signal is modulated.

While the order of addition of the reagents may be varied widely, there will be certain preferences depending on the nature of the assay. The simplest order of addition is to add all the materials simultaneously. Alternatively, the reagents can be combined wholly or partially sequentially. In the latter circumstance the sample and various agents utilized in the present invention may be combined other than concomitantly (simultaneously). Thus, one or more of the sample and reagents may be combined with one or more of the remaining agents to form a subcombination. Alternatively, the reagents may be added sequentially.

The following discussion is by way of illustration and not limitation as to the order of combining the sample and the reagents. In one approach the sample and a binding partner for each of the analytes are combined in a medium. First reagents are added to the combination, one for each of the analytes. Each first reagent comprises a member of a signal producing system, a ligand and an analyte analog. A second reagent comprising a binding partner for the ligand also is added to the combination.

Accordingly, in the above embodiment of the present method, in a first step a binding partner for each of the analytes is combined in a suitable assay medium with the sample suspected of containing the analytes. The medium is usually an aqueous buffered medium at a moderate pH, generally that which provides optimum sensitivity in the present method. The aqueous medium may be solely water or may include from 0.01 to 80 or more volume percent of a cosolvent. The pH for the medium will usually be in the range of about 4 to 13, more usually in the range of about 5 to 10, and preferably in the range of about 6.5 to 9.5. The pH is generally selected to achieve optimum assay sensitivity and specificity. Among the factors that must be considered are the pH dependence of the rates of the reactions involved, the binding of binding members and the minimization of non-specific binding, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the method in accordance with the present invention. For example, in addition to buffers the medium may comprise stabilizers for the medium and for the reagents employed. Frequently, in addition to these additives, proteins may be included, such as albumins; organic solvents such as formamide; quatemary ammonium salts; polyanions such as dextran sulfate; surfactants, particularly non-ionic surfactants; binding enhancers, e.g., polyalkylene glycols; or the like.

Binding partners for each of the analytes are generally components capable of specific binding to the particular analytes of interest. The binding partner may be a protein, which may be an antibody or an antigen. The binding partner may be a member of a specific binding pair ("sbp member"), which is one of two different molecules, having an area on the surface or in a cavity which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme—substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

Preferred binding partners are antibodies. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

In a next step of the aforementioned embodiment of a method of the invention, a first reagent may be added to the medium comprising the combination of the sample and the binding partner for each of the analytes. The first reagent comprises a member of a signal producing system, a ligand and an analyte analog.

Ligands include any organic compound for which a receptor naturally exists or can be prepared. The ligands may be selected from the ligands mentioned earlier in the discussion of the analyte. Preferably, the ligand is a small molecule, that is, a compound of molecular weight less than 2000, usually less than 1500, preferably, 100 to 1000, more preferably, 300 to 600. The small molecule is usually a small organic molecule such as, for example, haptens including drugs, dyes such as, e.g., fluorescein, rhodamine and the like, biotin, tetracycline, folate, B12 and so forth. The small molecule can provide a means for attachment of the components of the first reagent.

An analyte analog is a modified analyte, usually of a molecular weight greater than 100, which can compete with the analogous analyte for a receptor, the modification providing means to join a analyte analog to another molecule. The analyte analog will usually differ from the analyte by more than replacement of a hydrogen with a bond that links the analyte analog to a hub or label, but need not. The analyte analog can bind to the receptor in a manner similar to the analyte. The analog could be, for example, an antibody directed against the idiotype of an antibody to the analyte.

The analyte analog and the ligand will usually be separate moieties such as, for example, drug analogs and a small molecule. However, they may also represent different portions of the same group. Thus, a group might be constructed that binds to two different antibodies but only one of the antibodies is able to bind to the analyte. This situation is not uncommon. Antibodies not infrequently recognize a bound hapten but are unable to recognize the free hapten because they bind in part to the group linking the hapten to a label. Thus, the present method can be carried out with standard analyte-label conjugates provided that an antibody is available that binds only to the analyte analog along with an antibody that binds both the analyte analog of the conjugate and the analyte. However, when the assays as constructed in this way, it will usually be necessary to use a different analyte analog and a corresponding specific binding receptor for each member of a combined screening assay. For this reason the preferred approach for screening assays is to construct conjugates that have a ligand that is common to all the members of the combination bound to an analyte analog which is specific for each assay.

The signal producing system may have one or more components, at least one component being a label. A number of signal producing systems may be employed to achieve the objects of the present invention. The signal producing system generates a signal that relates to the presence of an analyte in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Exemplary signal-producing systems are described in U.S. Pat. No. 5,508,178 (Rose, et al.), the relevant disclosure of which is incorporated herein by reference.

As mentioned above, the label is a member of the signal producing system. Usually, the label is conjugated to one of the other members of the first reagent, i.e., the ligand or the analyte analog, or the label is associated with a matrix as discussed below. The label is capable of being detected directly or is detectable through a specific binding reaction that produces a detectable signal. The label can be isotopic or non-isotopic, usually non-isotopic, and can be a catalyst, such as an enzyme, a polynucleotide coding for a catalyst, promoter, dye, fluorescent molecule., chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The first reagent is a conjugate, i.e., a molecule comprised of two or more components bound together, optionally through a linking group, to form a single structure. The binding can be either covalent attachment such as by a direct connection, e.g., a chemical bond, between the components or between the components and a linking group or non-covalent attachment involving specific binding between complementary sbp members that are attached to components. The member of the signal producing system can be conjugated to another molecule such as the analyte analog or the ligand or both. Alternatively, the member of the signal producing system can be conjugated to the analyte analog, which in turn is conjugated to the ligand. Other conjugations are also contemplated. The member of the signal producing system may be associated with a matrix as discussed below The procedures employed for the conjugation are well-known in the art. Typically, for covalent attachment, one or more of the components contains a functional group suitable for attachment to one or more of the other components. The functional groups suitable for attaching the components or the first reagent are usually carbonyl functionalities, both oxocarbonyl, e.g., aldehyde, and non-oxocarbonyl (including nitrogen and sulfur analogs) e.g., carboxy, amidine, amidate, thiocarboxy and thionocarboxy. Alternative functionalities of oxo include active halogen, diazo, mercapto, olefin, particularly activated olefin, amino, phosphoro and the like. Of particular interest are activated esters or alkylating agents. Details of techniques for attaching molecules to one another are well known in the art. See, for example, Matthews, et al., *Anal, Biochem.* (1985) 151:205–209; Engelhardt, et al., European Patent Application No. 0302175 and U.S. Pat. No. 3,817,837, the relevant disclosure of which is incorporated herein by reference in its entirety.

As mentioned above, a linking group may be involved in the covalent linkage between molecules. The linking group will vary depending upon the nature of the components being linked. Functional groups mentioned above that are normally present on or are introduced on one or more components are employed for linking these materials. The linking groups may be a chain of from 1 to 100 atoms, usually from about 1 to 70 atoms, preferably 1 to 50 atoms more preferably 1 to 20 atoms, each independently selected from the group normally consisting of carbon, oxygen, sulfur, nitrogen, halogen and phosphorous. The number of heteroatoms in the linking groups will normally range from about 0 to 20, usually from about 1 to 15, more preferably 2 to 6. The atoms in the chain may be substituted with atoms other than hydrogen.

As a general rule, the length of a particular linking group can be selected arbitrarily to provide for convenience of synthesis and the incorporation of any desired group. The shortest chain linking the ligand and analyte analog in the conjugate will usually be less than 20 atoms, more frequently less than 10 atoms, and will preferably be as short as can be synthesized by convenient methods, often 2 to 6 atoms. In this regard it is important to keep in mind that the ligand and the analyte analog in the first reagent should be closely associated so that the binding of the binding partner for the analyte to the analyte analog blocks binding to a receptor. Thus, the length of the linking group is dependent on this principle.

The linking groups may be aliphatic or aromatic. When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or $\alpha$-, $\beta$-unsaturated ester, these functionalities will be linked to amine groups, carboxyl groups, active olefins, alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Various linking groups are well known in the art; see, for example, Cautrecasas, *J. Biol. Chem.* (1970) 245:3059.

As mentioned above, one or more of the components of the reagents may be attached together non-covalently. For example, a small organic molecule such as, for example, biotin including bis-biotin, fluorescein or the like may be incorporated into one of the components and the other component may be linked to a binding partner for the small organic molecule such as, for example, respectively, streptavidin, anti-fluorescein or the like. The binding of the binding partners results in the non-covalent attachment of the components to one another.

In a next step of the above embodiment of a method of the invention, a second reagent is added to the medium, which now contains the first reagent, the sample and a binding partner for each of the analytes. The second reagent comprises a binding partner for the ligand. The binding partners are discussed generally hereinabove.

One or more incubation periods may be applied to the medium at this point and/or at one or more intervals including any intervals between addition of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 6 hours, usually, from about 2 seconds to 1 hour, more usually, about 1 to about 5 minutes. The time period depends on the temperature of the medium and the rate of binding of the various reagents, which is determined by the association rate constant, the concentration, the binding constant and dissociation rate constant.

The concentration of analytes to be detected will generally vary from about $10^{-5}$ to $10^{-17}$ M, more usually from about $10^{-6}$ to $10^{-14}$ M. In general, a predetermined cut-off level is established for each analyte suspected of being in a sample. The particular predetermined cut-off level generally is determined on an analyte by analyte basis. Those skilled in the art are well aware of the factors relating to the selection of predetermined cut-off levels. For example, for many drugs of abuse, the cut-off levels are determined by SAMSA, an agency of the Department of Health and Human Services. The nature of the signal producing system may be a consideration in determining the predetermined cut-off levels of some analytes. Another consideration is that the expected variation in concentration of the analytes that is of significance should provide an accurately measurable signal difference.

Considerations such as the nature of the signal producing system and the nature of, and predetermined cut-off levels for, the analytes normally determine the concentrations of the various reagents. The final concentration of each of the reagents will normally be determined empirically to optimize the sensitivity of the method. The concentration of the first reagent is usually sufficiently high to permit detection of a signal, usually at least 10 times higher than the detection limit. The concentration of the second reagent is usually sufficiently high to bind at least 15, preferably at least 10%, more preferably at least 90%, of the first reagent in the absence of any binding partners for the analyte. The concentration of the binding partners for each of the analytes is usually sufficient to bind at least 1%, preferably at least 10%, more preferably, at least 90%, of the first reagent.

As mentioned above, the binding of the second reagent to the ligand alters the amount of signal produced by the member of a signal producing system. In this way a change such as, for example, a predetermined increased, in the amount of signal is produced if one or more of the analytes are present in the sample. The medium is examined for the presence and amount of signal produced by the signal producing system. The present and amount of signal is related to the presence of one or more of the analytes in the sample. In the present methods a change in signal is observed if one of more of the analytes is present in the sample above predetermined cut-off levels for the analytes. The nature of the examination of the medium depends on the type of method, i.e., homogeneous or heterogeneous, the type of signal expected to be produced, and the like. The examination includes providing any remaining members of the signal producing system including agents for activation of a member of the signal producing system. In a homogeneous approach the medium is examined directly for the presence of signal without a separation step. In a heterogeneous approach the medium generally is separated from other reaction components and either the medium or the separated components or both are examined for the presence of signal.

Activation of the signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems no agent for activation is necessary such as those systems that involve a label that is a radioactive label, an enzyme, and so forth. For enzyme systems addition of a substrate and/or a cofactor may be necessary.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, an absorption spectrometer, luminometer, chemiluminometer, actinometer, photographic instrument, and the like. The presence and amount of signal detected is related to the presence and amount of any analyte present in a sample above the predetermined cut-off level. Temperatures during measurements generally range from about 10° to about 70° C., more usually from about 20° to about 45° C., more usually about 20° to about 25° C. In one approach standard curves are formed using known concentrations of the analytes to be screened. Calibrators and other controls may also be used.

The methods disclosed herein are less expensive and faster than known methods because it is only necessary to carry out one assay per sample. The present invention avoids the difficulty of producing multiple independent signals. In the method of the invention, only one signal is produced in the assay. The intensity of the signal exceeds a certain threshold and indicates the presence, above its predetermined cut-off level, of one of the target analytes.

When an analyte of the plurality of suspected analytes affects an increase in signal, the present method offers an additional advantage. Negative signals, i.e., the signals that occur in the absence of an analyte, are added together when separate assays are combined, but the assay response for a given analyte, at best, remains unchanged. Combined assays therefore have a reduced ratio of their modulated signal to their negative signal that limits their sensitivity and reliability.

This problem is especially severe if assays are combined that have high negative signals that decrease with increasing amounts of, for example, drug analyte present. For example, if the maximum possible signal is 100 and the signal is reduced 10% upon adding a predetermined or cut off level of the drug, the ratio of the signal modulation to the negative signal is 10%. A combination of six such assays would have a negative signal of 600, but the signal modulation would still be 10% and the ratio would then be only 1.67%. On the other hand, when the present methods provide an increase in signal, low negative signals are realized, which increase with drug concentration. For example, if the maximum possible signal were again 100, the signal modulation at the cut off was again 10, but the negative signal was 10 instead of 100, the ratio of the signal modulation to the negative signal would be 100%. Upon combining six such assays, the negative signal would increase to 60 and the modulated to negative signal ratio would be 16.7%, which is above that for an individual assay in which the signal decreases with drug concentration.

In certain embodiments of the present invention, the first reagent or the second reagent or both may be associated with, e.g., bound to, a matrix, that is, a support comprised of an organic or inorganic, solid or fluid, water insoluble material, which may be transparent or partially transparent. The matrix can have any of a number of shapes, such as particle, including bead, film, membrane, tube, well, strip, rod, and the like. The surface of the matrix is, preferably, hydrophilic or capable of being rendered hydrophilic. The body of the matrix is, preferably, hydrophobic. The matrix may be suspendable in the medium in which it is employed. Examples of suspendable matrices in accordance with the present invention, by way of illustration and not limitation, are polymeric materials such as latex, lipid bilayers or liposomes, oil droplets, cells and hydrogels. Other matrix compositions include polymers, such as nitrocellulose, cellulose acetate, poly(vinyl chloride), polyacrylamide, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials.

Binding of components to the matrix may be direct or indirect, covalent or non-covalent and can be accomplished by well-known techniques, commonly available in the literature, as discussed above. See, for example, "Immobilized Enzymes," Ichiro Chibata, Halsted Press, New York (1978) and Cuatrecasas, *J. Biol. Chem.*, 245:3059 (1970). The surface of the matrix will usually be polyfunctional or be capable of being polyfuncuonalized or be capable of binding to an sbp member, or the like, through covalent or specific or non-specific non-covalent interactions. Such binding is indirect where non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above).

In a particular embodiment the matrix is a particle. The diameter of the particle is at least about 20 nm and not more than about 20 microns, usually at least about 40 nm and less than about 10 microns, preferably from about 0.10 to 2.0 microns diameter, normally having a volume of less than 1 picoliter. The particle may have any density, but preferably of a density approximating water, generally from about 0.7 to about 1.5 g/ml. The particles may or may not have a charge, and when they are charged, they are preferably negative. The particles may be solid (e.g., comprised of organic and inorganic polymers or latex), oil droplets (e.g., hydrocarbon, fluorocarbon, silicon fluid), or vesicles (e.g., synthetic such as phospholipid or natural such as cells and organelles). The solid particles can be comprised of polystyrene, polyacrylamide, homopolymers and copolymers of derivatives of acrylate and methacrylate, particularly esters oand amides, silicones and the like.

Oil droplets are water-immiscible fluid particles comprised of a lipophilic compound coated and stabilized with an emulsifier that is an amphiphilic molecule such as, for example, phospholipids, sphingomyelin, albumin and the like that exist as a suspension in an aqueous solution, i.e. an emulsion. Emulsions comprising oil droplets can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonicafion or vortexing. Illustrative lipophilic compounds include hydrocarbon oils, halocarbons including fluorocarbons, alkyl phthalates, trialkyl phosphates, triglycerides, etc. The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety).

Liposomes are microvesicles comprised of one or more lipid bilayers having approximately spherical shape. The liposomes have a diameter that is at least about 20 nm and not more than about 20 microns, usually at least about 40 nm and less than about 10 microns. Preferably, the diameter of the liposomes will be less than about two microns so as to limit settling or floatation. Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 discloses a method of extruding liposomes under pressure through a uniform pore-size membrane to improve size uniformity.

Latex particles signifies a particulate water suspendable water insoluble polymeric material usually having particle dimensions of 20 nm to 20 mm, more preferably 100 to 1000 nm in diameter. The latex is frequently a substituted polyethylene such as polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Noncrosslinked polymers of styrene and carboxylated styrene or styrene funcbonalized with other active groups such as amino, hydroxyl, halo and the like are preferred. Frequently, copolymers of substituted styrenes with dienes such as butadiene will be used.

In certain embodiments of the present invention first and second labels are employed and comprise a label pair. These label pairs may be, for example, a singlet oxygen generator or sensitizer and chemiluminescent reactant pair, an enzyme pair wherein a product of the first enzyme serves as a substrate for the second enzyme and a luminescent energy donor and acceptor pair, e.g., an energy donor or acceptor and a fluorescent compound. The signal will usually be initiated by and/or detected as electromagnetic radiation and will preferably be luminescence such as chemiluminescence, fluorescence, electroluminescence or phosphorescence.

Examples of chemiluminescent reactants or chemiluminescers, by way of illustration and not limitation, are olefins capable of reacting with singlet oxygen, e.g., to form hydroperoxides or dioxetanes, stable dioxetanes that can be activated with base or an enzyme, acetylenes that can react with singlet oxygen to form diketones, hydrazones or hydrazides that are activated with a peroxide and that can form azo compounds or azo carbonyls such as luminol, chemiluminescent enzyme substrates such as luciferin, aromatic compounds that can form endoperoxides, etc. The chemiluminescers can produce any detectable signal upon reaction with singlet oxygen.

In general, olefins of interest are those that undergo a chemical reaction upon reaction with singlet oxygen to form a metastable reaction product, usually a dioxetane or endoperoxide, which is capable of decomposition with the simultaneous or subsequent emission of light, usually within the wavelength range of 250 to 1200 nm. The dioxetanes may be luminescent alone or in conjunction with a fluorescent energy acceptor. Enol ethers are examples of such olefins. Enamines are another example of such olefins. Preferred are electron rich olefins usually containing electron-donating groups. Exemplary of such electron rich olefins are enol ethers, enamines, 9-alkylidene-N-alkylacridans, arylvinylethers, 1,4-dioxenes, 1,4-thioxenes, 1,4-oxazines, arylimidazoles, 9-alkylidene-xanthanes and lucigenin.

The luminescence produced upon reaction of the olefins of interest with singlet oxygen will preferably be at wavelengths above 300 nanometers, preferably above 500 nanometers, and more preferably above 550 nm. Compounds that absorb light at wavelengths beyond the region where the sample components contribute significantly to light absorption will be of particular use in the present invention. The absorbance of serum drops off rapidly above 500 nm and becomes insignificant above 600 nm. Luminescence above 550 nm is of particular interest. However, luminescence at shorter wavelengths is useful when interference absorbance of the sample is absent. Preferably, the chemiluminescent olefins will absorb light at less than about 400 nm to permit convenient handling in room light without the risk of inadvertently producing singlet oxygen by photosensitization.

Examples of suitable electron rich chemiluminescent olefins are set forth in U.S. Pat. No. 5,618,732, the disclosure of which is incorporated herein by reference. Such olefins generally have an electron-donating group in conjugation with the olefin.

The chemiluminescent compound may be associated with a matrix such as a particle as described above. As used herein, the term "associated with" includes association through covalent or non-covalent binding or through incorporation into the matrix. In this embodiment the primary requirement of the matrix is that it permit the diffusion of singlet oxygen therein at least to the proximate location of the incorporated chemiluminescent compound. The chemiluminescent compound may be incorporated into the matrix either during or after the preparation of the matrix. The chemiluminescent compound is usually chosen to dissolve in the matrix but may be covalently attached to the matrix. The chemiluminescent compounds, when not covalently attached, are usually hydrophobic to reduce their- ability to dissociate from the matrix. In general, the matrix composition is chosen so as to favor association of the label reagent with the matrix. The amount of chemiluminescent compound associated with or incorporated into the matrix for purposes of the present invention depends upon a number of factors such as, for example, the nature of the chemiluminescent compound and the matrix. The chemiluminescent compound is present in the matrix in an amount necessary to maximize the signal produced in accordance with the invention, i.e., to provide the highest signal to background in an assay. Generally, the amount of chemiluminescent compound is determined empirically and is usually about from $10^{-8}$ to 1M, preferably, from $10^{-5}$ to $10^{-2}$ M, more preferably, $10^{-3}$ to $10^{-1}$ M.

A sensitizer is a molecule, usually a compound, for generation of singlet oxygen. Preferably, the sensitizer is a photosensitizer. However, other sensitizers include, by way of example and not limitation, other substances and compositions that can produce singlet oxygen with or, less preferably, without activation by an external light source. Thus, for example, molybdate ($MoO_4$=) salts and chloroperoxidase and myeloperoxidase plus bromide or chloride ion (Kanofsky, J. Biol. Chem. (1983) 259:5596) have been shown to catalyze the conversion of hydrogen peroxide to singlet oxygen and water. Either of these compositions can, for example, be included in particles to which is bound an sbp member and used in the assay method wherein hydrogen peroxide is included as an ancillary reagent, chloroperoxidase is bound to a surface and molybdate is incorporated in the aqueous phase of a liposome. Also included as photosensitizers are compounds that are not true sensitizers but which on excitation by heal, light, ionizing radiation, or chemical activation will release a molecule of singlet oxygen. The best known members of this class of compounds includes the endoperoxides such as 1,4-biscarboxyethyl-1,4-naphthalene endoperoxide, 9,10-diphenylanthracen-9,10-endoperoxide and 5,6,11,12-tetraphenyl naphthalene 5,12-endoperoxide. Heating or direct absorption of light by these compounds releases singlet oxygen.

Photosensitizers are sensitizers for generation of singlet oxygen usually by excitation with light. The photosensitizer can be photoactivatable (e.g., dyes and aromatic compounds) or chemi-activated (e.g., enzymes and metal salts). When excited by light the photosensitizer is usually a compound comprised of covalently bonded atoms, usually with multiple conjugated double or triple bonds. The compound should absorb light in the wavelength range of 200–1100 nm, usually, 300–1000 nm, preferably, 450–950 nm, with an extinction coefficient at its absorbance maximum greater than 500 $M^{-1}$ $cm^{-1}$, preferably, 5000 $M^{-1}$ $cm^{-1}$, more preferably, 50000 $M^{-1}$ $cm^{-1}$, at the excitation wavelength. The lifetime of an excited state produced following absorption of light in the absence of oxygen will usually be at least 100 nanoseconds, preferably, at least 1 millisecond. In general, the lifetime must be sufficiently long to permit energy transfer to oxygen, which will normally be present at concentrations in the range of $10^{-5}$ to $10^{-3}$ M depending in the medium.

Photosensitizers that are to be excited by light will be relatively photostable and, preferably, will not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures. Typical photosensitizers include acetone, benzophenone, 9-thioxanthone, eosin, 9,10-dibromoanthracene, methylene blue, metalloporphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment, for example, to an sbp member. Examples of other photosensitizers that may be utilized in the present invention are those that have the above properties and are enumerated in N. F. Turro, "Molecular Photochemistry" page 132, W. A. Benjamin Inc., N.Y. 1965. The photosensitizers are preferably relatively non-polar to assure dissolution into a lipophilic member when the photosensitizer is incorporated in an oil droplet, liposome, latex particle, etc.

In the embodiment of the invention wherein a sensitizer and chemiluminescer are employed as the label pair, the luminescence or light produced in the method can be measured visually, photographically, actinometrically, spectrophotometrically or by any other convenient means to determine the amount thereof, which is related to the presence of one or more of the analytes in the medium. Usually, light emitted from the label pair is measured while the assay reagents are present in the assay medium, for example, by means of a luminometer or a photosensitive material.

In some embodiments of the present invention, a fluorescent energy acceptor may be employed. The fluorescent energy acceptor is a chromophore having substantial absorption higher than 310 nm, normally higher than 350 nm, and preferably higher than about 400 nm. The width of the emission band at half peak height will usually be less than 100 nm, preferably less than 50 nm, more preferably, less than 25 nm. The fluorescent energy acceptor should be capable of absorbing light emitted by the fluorescent energy donor such as a fluorescent compound. Preferably, the absorption maximum of the fluorescent energy acceptor should be at similar wavelength as the emission maximum of the donor. A high extinction coefficient is desirable, usually in excess of 10, preferably in excess of $10^3$, and particularly preferred in excess of $10^4$. The fluorescent energy acceptor preferably has a high fluorescence quantum yield, usually at least 0.1, preferably greater than 0.4.

Preferred fluorescent energy acceptors are long wavelength, preferably hydrophobic, emitters including polycyclic aromatic hydrocarbons such as anthracenes, e.g., bisphenylethynylanthracene; coumarins; naphthacenes; phthalocyanines; squaraines, bis-(4-dimethlyaminophenyl) squaraine; porphyrins; polyacetylenes, oxazine dyes; rare earth chelates, especially, Eu, Tb and Sm, and the like. In general these dyes act as acceptors in energy transfer processes and preferably have high fluorescent quantum yields and do not react rapidly with singlet oxygen. They can be incorporated into matrices together with the donor. Hydrophilic fluorescent dyes may also be used, particularly cyanine dyes, xanthenes such as fluorescein and Texas red, and umbelliferones.

A number of different molecules useful as the fluorescent energy acceptor are described by Ullman, et al. in U.S. Pat. Nos. 4,261,968, 4,174,384, 4,199,559 and 3,996,345, at columns 8 and 9, the relevant portions of which are incorporated herein by reference.

In one embodiment the fluorescent energy acceptor may be formed as a result of a compound that reacts with singlet oxygen to form a fluorescent compound or a compound that can react with an auxiliary compound that is thereupon converted to a fluorescent compound. The fluorescent energy acceptor may be incorporated as part of a compound that also includes the chemiluminescer. For example, the fluorescent energy acceptor may include a metal chelate of a rare earth metal such as, e.g., europium, samarium, tellurium and the like. These materials are particularly attractive because of their sharp band of luminescence.

A typical assay protocol is described next by way of example and not limitation. The first reagent is a conjugate of a small molecule, an analyte analog, and a particle with which is associated a chemiluminescent compound. The second reagent is a particle reagent comprising an antibody that binds to the small molecule bound to a particle with which is associated a sensitizer. In the method the analyte binds to an antibody, which in the absence of analyte inhibits binding of the sensitizer and chemiluminescer particles. Activation of sensitizer particles with light results in the formation of singlet oxygen, which is channeled to the chemiluminescent compound only when the sensitizer and the chemiluminescer particles are bound to each other. Sample to be screened for the presence of one or more analytes is combined in a suitable medium with antibodies for each of the analytes suspected of being in the sample. If one or more of the analytes are present, their respective antibodies bind them. For analytes that are absent, the antibodies for those respective analytes remain unbound. First reagents are added to the medium, one for each of the suspected analytes. The analyte analogs on the particles are allowed to react with their respective unbound antibodies. Then, the second reagent is added. If an analyte is present, the corresponding antibody will be bound thereto and signal is emitted because the chemiluminescent compound and the sensitizer come into close proximity. On the other hand, if an analyte is absent, the corresponding antibodies bind with the conjugate on the first reagent and no signal production will occur relating to that analyte. Accordingly, an increase in signal is observed. The amount of signal is measured and related to the amount of signal corresponding to that obtained for predetermined cut-off levels for the respective analytes. The method gives a yes or no answer. If one or more of the analytes is present above the predetermined cut-off levels, a yes answer is obtained.

Another aspect of the present invention relates to kits useful for conveniently performing a screening assay method of the invention. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents.

In one embodiment a kit of the present invention comprises in packaged combination (i) an antibody for each of the drugs, (ii) for each of the drugs, a first reagent comprising a first label, a ligand and a drug analog, and (iii) a second reagent. The second reagent comprises a second label and an antibody for the ligand. The first label and the second label are capable of interacting in close proximity to produce a predetermined increased amount of signal if one or more of the drugs are present in the sample. The first label and the second label may be a sensitizer-chemiluminescer pair. The kit can further include other separately packaged reagents for conducting an assay such as ancillary reagents and so forth.

The relative amounts of the various reagents in the kits can be varied widely to provide for concentrations of the reagents that substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a Written description of a method in accordance with the present invention as described above.

The foregoing discussion is provided by way of illustration and not limitation to enable one skilled in the art to appreciate the scope. of the present invention and to practice the invention without undue experimentation. It will be appreciated that the choice of components, e.g., analytes, reagents, particles, other reagents and reaction conditions will be suggested to those skilled in the art in view of the disclosure herein and the examples that follow.

EXAMPLES

The invention is demonstrated further by the following illustrative examples. Parts and percentages recited herein are by weight unless otherwise specified. Temperatures are in degrees centigrade (° C.).

Melting points were determined on a Hoover capillary apparatus and are uncorrected. 'HNMR spectra were recorded on a Brucker WP-250 MHz or Brucker WP-300 MHz NMR spectrometer. Chemical shifts were reported in parts per million ($\delta$ 0.0). NMR multiplicities are recorded by use of the following abbreviations: s, singlet; d, doublet; t, triplet; m, multiplet; Hz, hertz. Infrared spectra were recorded on a Perkin-Elmer 297IR spectrometer. Desorption chemical ionization (C.I.) and electron ionization (E.I.) were done on a Varian-MAT 311A, double focusing high-resolution mass spectrometer. A Finnigan TSQ-70 or MAT-8230 was used for fast atom bombardment mass spectra (FAB/LSIMS). UV-visible absorption spectra were done on a HP 8452A diode array spectrophotometer. Fluorescence and chemiluminescence measurements were done on a Spex fluorolog spectrophotometer or a Perkin Elmer 650-40 spectrophotometer. Chemiluminescence measurements were performed on a custom built chemiluminometer fitted with 675 and 780 nm lasers as light sources.

Toluene was distilled over sodium under argon. Unless mentioned otherwise, all solvents were used without purification, and most reactions were carried out under argon. Silica gel used for flash chromatography was 230–400 mesh ASTM, purchased from Scientific Products while preparative plates (1000$\mu$) and analytical plates were purchased from Analtech.

C-28 thioxene was prepared as described below. 2-Chloro 9,10-bis(phenylethynyl) anthracene (1-CI-BPEA) and rubrene (5,6,11,12-tetraphenyl naphthacene) were purchased from Aldrich Chemical Co. Rubrene was recrystallized from methylene chloride and stored at 4° C. in a brown bottle prior to use. Silicon phthalocyanine was prepared as described below and phthalocyanine tetrasulfonates was obtained from Ultra Diagnostics, Inc. Carboxylate-modified polystyrene (latex) particles were purchased from Seradyn, Inc. The particles were 203±4.0 nM. The carboxyl parking area was 49.5 angstroms squared (0.09 milliequivalentslg). Solids were 10% (100 mg/ml).

2-ethoxyethanol was from Aldrich Chemical Co. and was redistilled under vacuum. Sodium hydroxide was 0.1 N. Isopropanol was from Aldrich Chemical Co.

The following abbreviations have the meanings set forth below:

Tris HCl—Tris(hydroxymethyl)aminomethane-HCl (a 10×solution) from BioWhittaker, Walkersville, Md.

BSA—bovine serum albumin from Sigma Chemical Company, St. Louis Mo.

g—grams mmol—millimolar

DMF—dimethyl formamide

THF—tetrahydrofuran

LSIMS—fast ion bombardment mass spectroscopy

NMR—nuclear magnetic resonance spectroscopy

TMSCl—tetramethylsilylchloride

MES—2-(N-morpholino)ethane sulfonic acid

Sulfo-SMCC—N-sulfosuccinimidyl-4-(N-maleimidomethyl)cyclohexane-1-carboxylate

CMO—carboxymethoxylamine.

THC—tetrahydrocannabinol

EDAC—1-ethyl-3-(3-dimethylaminopropyl) carbodiimide hydrochloride (Sigma Chemical Company)

TAPS—3-N-tris-(hydroxymethyl)methylamino propanesulfonic acid

Microgon—Minikros tangential flow filter apparatus from Microgon Inc., Laguna Beach, Calif.

The following reagents were purchased as indicated:

Sigma Chemical Company, St. Louis, Mo.

TRIZMA base (#T-1503), BSA (#A-7888), EDTA (#E-4884), Sucrose (#S-7903)

Pharmacia, Piscataway, N.J.

Dextran T-500 (#17-0320-02)

(Pierce, Rockford. Ill.

TWEEN 20® surfactant (#28320)

Mallinckrodt, St. Louis, Mo.

Sodium acetate trihydrate (#7364), Hydrochloric Acid (#2062) NaCl (#7851)

Aldrich Chemical Company, St. Louis, Mo.

$NaBH_3CN$ (#15,615-9), CMO (#C1,340-8),

Research Organics, Cleveland, Ohio

MES

Life Technologies, Rockville, Md.

Gentamycin Sulfate (#15750-011, 15750-029)

Scantibodies, Los Angeles, Calif.

HBR-1 (#3b484)

The University of Texas Southwestern Medicalgenter at Dallas

Patient urine samples positive for morphine and cocaine metabolite Rohm & Haas chemical Co. Philadelphia, Pa.

Kathon:

Aldrich Chemical Co., St. Louis Mo./Syva Division of Dade Behring Inc., San Jose, Calif.

Morphine, benzoylecgonine and THC

Assay Buffer: 0.05% Kathon, 1/320 HBR-1, 1 mg/ml BSA, 1 mg/ml, Dextran T-500, 0.1 mg/ml Gentamycin sulfate, 25 mM EDTA, 0.1M Tris, 0.3M NaCl (pH 8.4).

MES Buffer: 1M MES (pH 6.0)

Preparation of Reagents

Preparation of Antibodies

The following polyclonal antibody was produced by procedures as discussed below: anti-cocaine metabolite polyclonal antibody. Antiserum containing antibodies is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

The following monoclonal antibodies were produced by procedures discussed below: anti-morphine antibody (OCM M1 16C3), anti-THC antibody (MCAb 2-57) and anti-digoxin antibody (2H6). Monoclonal antibodies were produced according to the standard techniques of Kohler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of an non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In general, antibodies can be purified by known techniques such as chromatography, e.g., DEAE chromatography, ABx chromatography, and the like, filtration, and so forth.

Synthesis of C-28 Thioxene:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1 N aqueous NaOH (2x), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL), A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr and stirred for another 30 min. The resulting mixture was poured into a mixture of ice water (800 mL) and ethyl acetate (250 mL). The organic phase was separated and the aqueous phase was extracted with ethyl acetate (3x). The combined organic phases were washed with $H_2O$ (2x), brine and were dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (LSIMS ($C_{42}H_{69}NO_2$): $[M-H]^+$ 618.6, $^1H$ NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5N aqueous NaOH and was extracted with $CH_2Cl_2$ (3x). The combined organic layers were washed with saturated aqueous $NaHCO_3$ (2x) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.59 (60%) of the C-28 thioxene as an orange-yellow oil (LSIMS ($C_{44}H_{71}NOS$): $[M-H]^+$ 661.6, $^1H$ NMR (250 MHz, $CDCl_3$) was consistent with the expected C-28 thioxene product 2-(4-(N,N-di-($C_{14}H29$)-anilino)-3-phenyl thioxene.

Synthesis of Phthalocyanine Sensitizer

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely reacted, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued during the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask and concentrated sulfuric acid (500 mL) was added with stirring. The mixture was stirred for 4 hr. at 60° C. and was then carefully diluted with crushed ice (2000 g). The resulting mixture was filtered and the solid was washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (LSIMS: $[M-H]^+$ 364.2, absorption spectra: methanol: 674 nm (ε 180,000): toluene 678 nm, $^1H$ NMR (250 MHz, $CDCl_3$): δ: −2.4(m, 12H), −1.3(m, 12H), 0.2–0.9 (m, 54H), 1.8(s, 36H), 8.3(d, 4H) and 9.6 (m, 8H) was consistent with the above expected product.

Synthesis of Dextran Aldehyde

The procedure used to prepare dextran aldehyde was that described in U.S. Pat. No. 5,929,049 (R. Singh, et al.), the relevant disclosure of which is incorporated herein by reference.

Synthesis of Hydroxypropylaminodextran.

Hydroxypropylaminodextran was prepared by dissolving 100 g of Dextran T-500 (Pharmacia, Uppsala, Sweden) in 500 mL of water in a 3-neck round-bottom flask with a mechanical stirrer and dropping funnel. To the solution was added 45 g sodium hydroxide, 50 mg EDTA, 50 mg NaBH$_4$, 50 mg hydroquinone, and 200 g N-(2,3-epoxypropyl) phthalimide. The mixture was heated and stirred in a 90° C. water bath for two hours. A small aliquot was precipitated three times from methanol and analyzed by NMR. The appearance of a peak at 7.3–7.6 indicated incorporation of phthalimide. The main reaction mixture was precipitated by addition to 3.5 L of methanol, after which solid was collected. The phthalimide protecting group was removed by dissolving the product above in 500 mL of 0.1 M acetate buffer, adding 50 mL of 35% hydrazine, and adjusting the pH to 3.5. The mixture was heated at 80° C. for 1 h, the pH was re-adjusted to 3.2, and the mixture was heated for an additional half hour. An aliquot was precipitated three times in methanol. NMR showed that the phthalimide group was no longer present. The reaction mixture was neutralized to pH 8 and stored at room temperature.

The product was purified by tangential flow filtration using a 50,000 molecular weight cut-off filter, washing with water, 0.01 M HCl, 0.01 M NaOH, and finally water. The product solution was concentrated by filtration to 700 mL then lyophilized. Determination of reactive amines using trinitrobenzenesulfonate gave about 1 amine per 16 glucose residues.

Preparation of Sensitizer Beads

Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 40 mg of silicon tetra-t-butyl phthalocyanine prepared as described above was added; the beads were stirred for 5 minutes more. At this point 1.0 mL of 0.1N NaOH was added slowly over 5 minutes. During all the additions, the oil bath temperature was maintained at 105° C. The oil bath temperature was slowly allowed to drop to room temperature over 2 hours. After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

Preparation of Streptavidin-coated Sensitizer Beads

A 2.5 L suspension of dyed sensitizer beads (6 mg/mL) in TAPS buffer (50 mM, pH 8.30) was prepared. Sensitizer beads (33 mg/mL) (455 mL) were added to 2.05 L of TAPS buffer contained in a three-necked 3.0 L round bottomed flask. The pH of the suspension was adjusted to 8.3 by addition of 0.1 N HCl or 0.1 N NaOH. The suspension was stirred at 350–400 rpm and 75 mL of TAPS containing 0.6 mL of hydrazine was added. STUT (6.0 g) (O-(N-succinimidyl)-N,N, N',N'-tetramethyluronium tetrafluoroborate, Fluka Chemical Co., Milwaukee, Wis.) was added slowly to the above mixture in four equal aliquots dissolved in 8 mL of DMSO at 15 minute intervals. The pH of the mixture was adjusted to 8.30 after each addition of an aliquot. The mixture was stirred at room temperature for an additional 2 hr after addition of the last aliquot. The beads were purified by Microgon (Microgon Inc., Laguna Beach, Calif.).

A filtered dextran solution (275 mL, 40 mg/mL, 11.0 g) was transferred to a 3-necked, round bottom flask and a 20 mg/mL (275 mL) suspension of the beads prepared above in water was added dropwise to the stirring dextran solution. The pH of the reaction mixture was adjusted to 5.0 if necessary. The reaction mixture was stirred for an additional 30 minutes and then was transferred to a 1.0 L glass bottle and was shaken for 17 hr. at 50° C. The beads were washed Microgon.

A solution of streptavidin at 10–12 mg/mL (75-62.5 mL) in an acetate buffer (pH 5.0, 0.2 M) was prepared and the beads prepared above were added slowly with stirring to the solution at 19.0 mg/mL (79 mL). The reaction mixture was stirred for 30–60 minutes. A solution of sodium cyanoborohydride (150 mg in 10 mL) in water was added to the above reaction mixture and the pH was adjusted to 5.0. The reaction container was covered with aluminum foil and shaken at 100–150 rpm at 37° C. for 48–60 hrs. To this reaction medium was added 2.0 mL of a 1.0 M solution of CMO at pH 5.0 prepared by adding 10 N sodium hydroxide to 2.19 g of CMO hemihydrochloride dropwise. The reaction medium was incubated at 37° C. for 4–8 hr and the particles were washed by Microgon.

Preparation of Conjugate

For each of the drugs to be included in the screening assay, a separate bis-biotin-drug-digoxin conjugate (morphine-bis-biotin conjugate, benzoylecgonine-bis-biotin conjugate and THC-bis-biotin conjugate) was synthesized according to the following procedure:

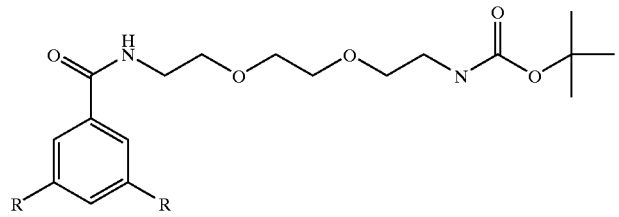

1

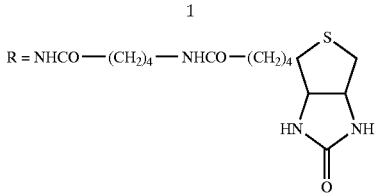

-continued
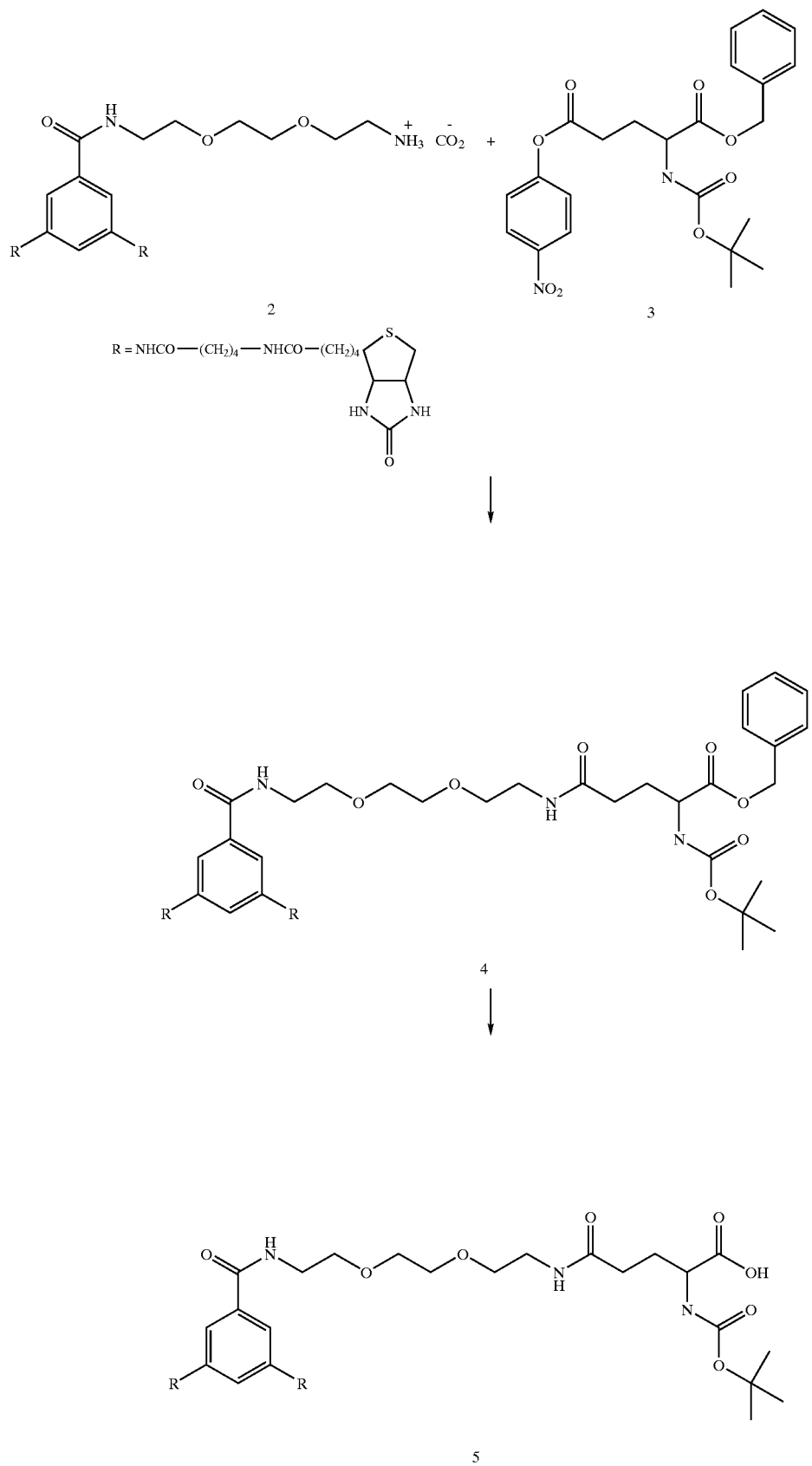

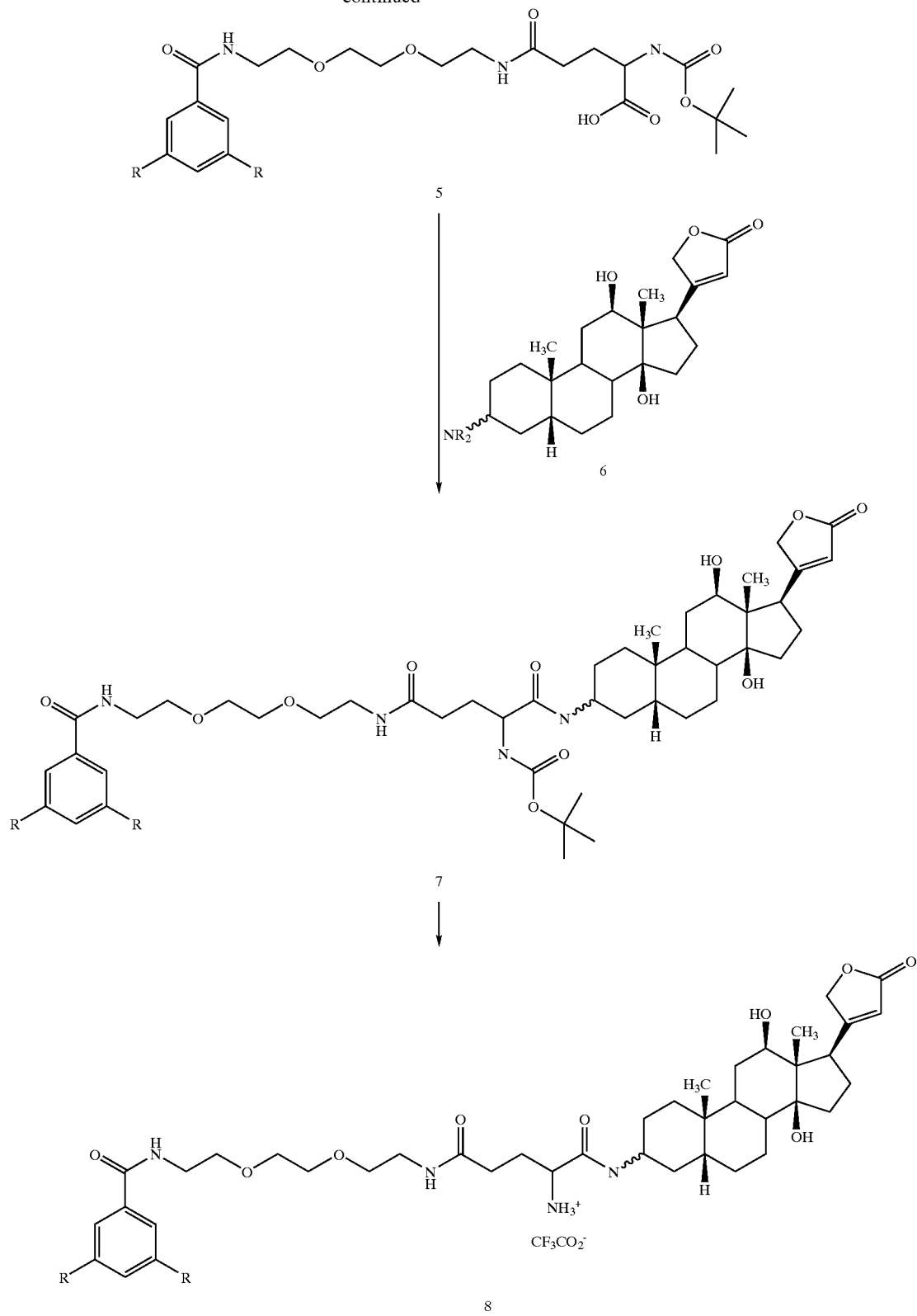

Preparation of 7 a Bisbiotin Derivative Linked to Aminodigoxigenin:

In a 250 ml round bottom flask equipped with a magnetic stirring bar was placed 775 mg of N-t-Boc bisbiotin amine 1 (dried at 100° C., 0.5 mm, 5 hr) and dichloromethane (20 ml). This was followed by dropwise addition of 10 ml anhydrous trifluoroacetic acid that caused dissolution and deprotection of 1 to compound 2. The trifluoroacetate salt 2 was precipitated with 100 ml of anhydrous diethyl ether. The solvent was decanted and the residue was separated and heated under vacuum at 45C for 30 minutes. The salt was then dissolved in the minimum amount of methanol. While the solution was vortexing, 40 ml of anhydrous diethyl ether was added to precipitate compound 2. The supernatant was decanted and the precipitate was separated and heated under vacuum (0.5 mm, 100C, 4 hr) to give 725 mg yield of compound 2. Aminobisbiotin trifluoroacetate salt 2 (725 mg, 0.75 mmoles), 10ml of anhydrous dimethylformamide and 0.5 ml of triethylamine were combined in a 250 ml round bottom flask equipped with a magnetic stirring bar. To this stirring solution was added (332 mg, 0.764 mmoles) of N-boc-L-glutamic acid-γ-N-hydroxysuccinimide ester α benzyl ester 3 (lot # 121363, item # A-2530, BaChem Bioscience). The reaction was stirred at ambient temperature for 1 hr. (TLC analysis, Analtech silica gel GF, 250μ plate, elutant 2:8 methanol—ethyl acetate). The reaction was then concentrated using a rotary evaporator at 35° C. The residue was then taken up into the minimum amount of methanol and was added dropwise to a vortexing solution of saturated sodium chloride (40 ml) in a glass centrifuge tube. The supernatant was then decanted and the white precipitate was washed with 3×30 ml of water and then was dried under vacuum (0.5 mm, 16 hr, over $P_2O_5$) to give 1.4 g yield of 4. Purification was accomplished using preparative thin layer chromatography of the semi-pure product 4. This material was dissolved in 4:6 methanol—dichloromethane and was applied to 16–20×20 cm 1000μ Analtech silica GF plates. After air drying, the plates were developed with 4:6 methanol—ethyl acetate. The product was isolated and extracted from silica gel with 400 ml 3:7 methanol—dichloromethane. The extract was concentrated on a rotary evaporator to give 4 as a white foam (610 mg, dried at 0.5 mm, 40° C.). The mass spectrometry resulted (instrument/ionization technique, VG 70SE/FAB) the molecular ion MNa+=1274.6. The benzyl ester 4 (600 mg, 480 mmoles) was converted to acid 5 using the following procedure. The ester 4 was dissolved in methanol (30 ml) and NaOH (10 ml, 0.5M) was then added and stirred for 16 hr at ambient temperature. The reaction was concentrated under vacuum to ~15 ml. The concentrate was placed in a glass centrifuge tube followed by addition of 35 ml of saturated sodium chloride. While vortexing, the pH was adjusted to 3.5 with concentrated hydrochloric acid. After centrifugation, the liquid was decanted and the precipitate was washed with 4×25 ml of distilled water to yield 540 mg of 5 (dried over $P_2O_5$, 0.5 mm, 100° C.). The mass spectrometry showed (instrument/ionization technique, VG 70SE/FAB) the molecular ion MH+=1162, MNa+1184. The bisbiotin carboxylic acid derivative 5 116 mg (0.10 mmoles), 23 mg (0.12 mmoles) of 1- ethyl—(3-dimethylaminopropyl) carbodiimide hydrochloride, 14 mg (0.12 mmoles) of N—hydroxysuccinimide and 1 ml of anhydrous dimethylformamide were combined and stirred under a dry atmosphere at ambient temperature for 16 hr. In a separate 25 ml round bottom flask were added 3 -αβ-amino desoxydigoxigenin (45 mg) 6, 1.5 ml of anhydrous dimethylformamide and 200 μl triethylamine. To the stirring solution at ambient temperature was added dropwise the above activated ester. After 30 min the reaction was concentrated on a rotary evaporator at 40° C. To the concentrate was added 30 ml of saturated sodium chloride solution. The supernatant was decanted, the solid was washed with 2×30 ml distilled water and the crude product was dried under vacuum at 40° C. The crude product was dissolved in methanol—dichloromethane and was applied to 4–20×20 cm 1000μ Analtech silica gel GF plates and developed with 1:1 methanol—ethyl acetate. The appropriate bands were isolated and extracted from silica gel with 3:7 methanol—dichloromethane and filtered. The filtrate was concentrated and dried at 45° C. under vacuum to give 100 mg of 7 (66%). The mass spectrometry indicated (instrument: ionization technique, VG 70SE/FAB) the molecular ion MH+=1534, MNa+=1556.

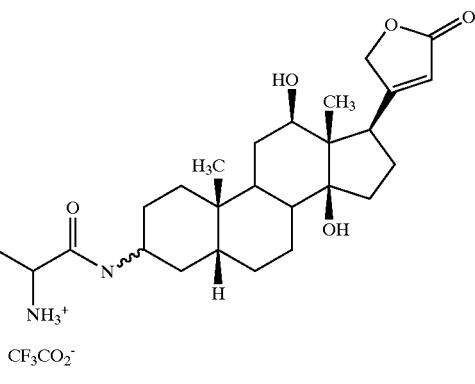

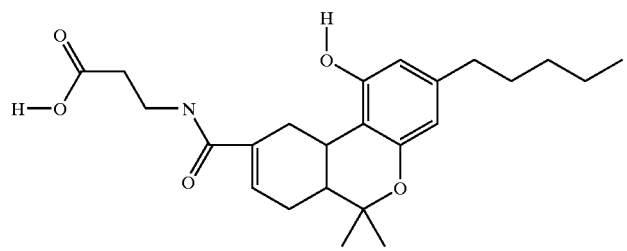

13

Preparation of 10 by Coupling of Morphine Hapten 9 to Bisbiotin Digoxigenin 8:

Into a 4 ml glass vial equipped with a magnetic stirring bar, was added 15 mg (.033 mmoles) of o—carboxymethyl morphine 9, 10 mg (.052 mmoles) of 1-ethyl—(3-dimethylaminopropyl) carbodiimide hydrochloride, 10 mg (.086 mmoles) of N—hydroxysuccinimide and 0.6 ml of anhydrous dimethylformamide. The reaction was stirred in a dry atmosphere at ambient temperature for 16 hr. To 50 mg of the t—boc bisbiotin digoxigenin derivative 7 in a 50 ml round bottom flask was added 6 ml of 1:1 dichloromethane trifluoroacetic acid. The mixture was stirred at ambient temperature for 10 minutes. The solvent was then removed using a rotary evaporator and the residue was dried at 35° C. for 30 minutes under vacuum. The residue was then dissolved in 5 ml of methanol and precipitated with ethyl ether. The precipitate was then dried as described above to give compound 8. The trifluoroacetate salt 8 was dissolved in 1.5 ml of anhydrous dimethylformamide and 100 μl of triethylamine. This mixture was then added dropwise to the above activated morphine hapten and stir for 5 hours at ambient temperature. The reaction was then concentrated on a rotary evaporator with heating at 35° C. The residue was then taken up into the minimum of methanol and was added dropwise to a 10 ml saturated aqueous sodium chloride. The mixture was stirred for 0.5 hours. The solvent was then decanted and the precipitate was dried under vacuum. The crude product was dissolved in methanol—dichloromethane and applied to a 2–20×20 cm 1000μ Whatman reverse phase $PKC_{18}$ plates. The plates were then developed with 2:8 water—methanol. The appropriate bands were collected and product was isolated by extraction from absorbent using vacuum filtration with 1:1 methanol—dichloromethane to give 10 as a white solid. The mass spectrometry showed (instrument: ionization technique, VG 70SE/FAB(+) with matrix TG/G) the molecular ion MH+=1759.

Preparation of 12 by Conjugation of Benzoecgonine Hapten 11 to Bisbiotin Dicoxigenin 8:

To a stirred solution of (0.027 mmoles) of the trifluoroacetate salt of bisbiotin digoxigenin conjugate 8 as described above was added 3.5 mL of anhydrous dimethylformamide, 50 μL triethylamine and a solution of 12 mg (0.034 mmoles) of p—isothiocyanatobenzoecgonine in 0.5 mL dimethylformamide. The reaction was stirred for 4 hours at ambient temperature followed by concentration (370C, 0.5 mm) and then by precipitation of the product by dropwise addition of the concentrate into 10 ml of saturated sodium chloride solution. The precipitate was then separated and dried. The crude product was purified using 2–20×20cm 1000μ Whatman $PLKC_{18}F$ plates, developed with 1:4:5 water—methanol—dichloromethane. The appropriate bands were isolated and extracted from the absorbent using 1:1 methanol—dichloromethane as described above to give 12 as a pale yellow solid. The mass spectrometry indicated (instrument: ionization technique, VG 70SE/FAB(+) with matrix TG/G) the molecular ion M=1780 MNa+=1802.

Preparation of 14 by Conjugation of 9-Carboxamidopropanoic Acid -11-nor $\Delta^B$ Tetrahydrocannabinol 13 to Bisbiotin Digoxigenin 8:

The β-alanine derivative of 9-carboxy 11-nor $\Delta^8$ tetrahydrocannabinol was activated by combining 10.3 mg (0.025 mmole) of 13, 3.1 mg (.027 mmoles) of N—hydroxysuccinimide and 5.6 mg (0.027 mmoles) of 1,3-dicyclohexylcarbodiimide in 1 ml of anhydrous tetrahydrofuran. The mixture was then stirred at ambient temperature for 16 hours in a dry atmosphere. To a stirring solution of (0.0167 mmoles) of the trifluoroacetate salt of bisbiotin digoxigenin conjugate 8 (prepared as previously described) in 3 ml of anhydrous dimethylformamide and 100 μl of triethylamine, was added dropwise the above activated tetrahydrocannabinol ester. The reaction was stirred for 16 hours at ambient temperature and then was concentrated by heating at 37° C. and under vacuum. The residue was dissolved in minimum amount of methanol and then was precipitated by dropwise addition to a stirring solution of 10 ml of saturated sodium chloride solution. The precipitate was dried and dissolved in minimum amount of methanol. The solution was then applied to a 20×20 cm 1000μ Analtech silica gel GF plate and was developed with 2:8 methanol—dichloromethane. The product was isolated from silica gel as previously described using 3:7 methanol—dichloromethane. The pure product 14 was characterized by mass spectrometry. Instrument: ionization technique, VG ZAB2-EQ/FAB(+) with matrix TG/G molecular ion MH+=1854.

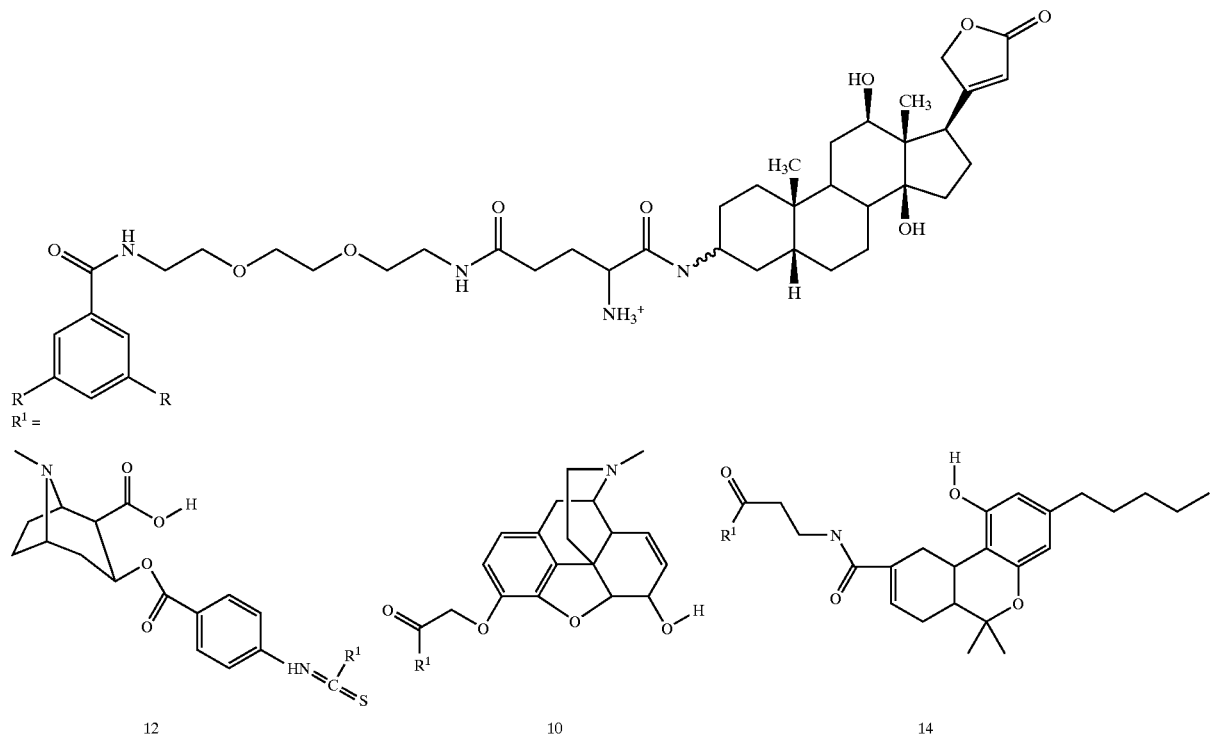

Preparation of First Reagent (Streptavidin-coated Sensitizer Beads with Attached Conjugate)

Each of the conjugates prepared as described above was attached to streptavidin-coated sensitizer beads prepared as described above using the following procedure.
1. A 2.06-mg aliquot of streptavidin-coated sensitizer beads (2155 streptavidin molecules per bead) was diluted into 4.12 ml assay buffer. ($3.91 \times 10^{11}$ beads)
2. Conjugate (1.0 mM) was diluted 1:100 to yield a working solution of $6.02 \times 110^{12}$ conjugates per µl. An aliquot of 64.4 µl of this solution was diluted to 4.12 ml with assay buffer.
3. The conjugate solution was then added dropwise (with constant stirring) to the bead solution. The result was a bead reagent with approximately 1000 conjugates per bead. These were stored at 4° C.
4. Separate drug-digoxin-bis-biotin-bead reagents were made for morphine, benzoyleogonine and THC.

Preparation of Chemiluminescer Bads

A 10% solution of carboxylated latex beads (120 mL) was heated to 93° C. in a three-neck round bottom flask, and then was mixed with 166 mL ethoxyethanol, 336 mL ethylene glycol, and 12 mL of 0.1 M NaOH. A mechanical stirrer and a thermometer were added and the mixture was brought to 95° C. with stirring and then was stirred for an additional 40 min. In a separate flask, 2.45 g of C-28 thioxene, 191.8 mg of 2-chloro-9,10-bis(phenylethynyl) anthracene, and 323.9 mg of rubrene were mixed in 264 mL of ethoxyethanol and the mixture was heated to 95° C. with stirring until dissolved. The dye solution was poured into the bead soluton and was stirred for 20 min. at 95° C. and then was allowed to cool slowly to about 47° C. and filtered through a 43 micron polyester filter. The beads were washed by tangential flow filtration using a Microgon apparatus with a 0.05 micron filter. After priming of the system with wash solvent (1:2 v/v ethoxyethanol:ethylene glycol), the dyed bead mixture was added. The mixture was concentrated to about 20 mg/mL and then was washed with 6 L of wash solvent and 4.8 L of 10% v/v ethanol in water adjusted to pH 10 with NaOH. The beads were concentrated to about 50 mg/mL during the wash, and then were finally stored at 4° C. protected from light. Final concentration was determined by weight after evaporating an aliquot to dryness.

Preparation of Chemiluminecser Beads Attached to Anti-Digoxin

A solution of 4 g of hydroxypropylaminodextran (prepared as described above) in 200 mL of 50 mM MES, pH 6±0.1 was subjected to Microgon filtration. To the filtered solution (150 mL) was added dropwise with stirring 150 mL of a 20 mg/mL suspension of chemiluminescer beads from above in 10% ethanol/water. Stirring was continued for 30 minutes. A solution of 1.2 g of EDAC in 15 mL of water was added dropwise with stirring to the above reaction mixture. The reaction mixture was protected from light and stirred overnight at room temperature.

A solution of dextran aldehyde prepared as discussed above (10 g/200 mL 50 mM MES, pH 6±0.1 was subjected to Microgon filtration using a module of 0.2 micron rated pore size. To the filtered solution (100 mL) was added dropwise a previously sonicated 25-mL aliquot of a 20 mg/mL suspension of the above chemiluminescer beads in 10 mM MES, 0.5 NaCl, pH 6. A total of 4 aliquots were added to the dextran aldehyde solution. Stirring was continued for 30 minutes. Then, a solution of 400 mg sodium borohydride in 10 mL water was added dropwise to the stirring bead mixture. The reaction mixture was protected from light and shaken at 37° C. for 40 to 60 hours. The beads were purified by Microgon washing.

Anti-digoxin antibody was attached to chemiluminescer beads prepared as described above.

Beads were prepared in 1.5 ml microfuge tubes. Reagents were added in the order and amounts as follows: 55 µl water, 50 µl 1 M MES (pH 6.0), 5 µl 10% TWEEN 20® surfactant, 100 µl beads (100 mg/ml), 280 µl anti-digoxin and 10 µl NaBH$_3$CN. Samples were vortexed after each addition.

3. After incubation, 20 µl 1.0 M CMO was added.
4, Incubation was continued at 4° C. overnight.
5. The bead solutions were layered on a 7 ml bed of 7% sucrose in 1M Tris buffer (pH 8.0) containing 0.1% gentamycin.
6. Beads were centrifuged at 12K and 10° C. for 30 min.
7. Supernatants were removed from the pelleted beads with Pasture pipettes.
8. Beads were resuspended in 5 ml 100 mM Tris buffer pH 8.0.
9. Steps 6 and 7 were repeated.
10. Beads (10 mg/ml) were resuspended in 100 mM Tris buffer pH 8.0 and were stored at 4° C.

Example 1

Screening Assay for Morphine and Cocaine Metabolite

The screening assay is a positive-response assay. In the first step of this assay, the sample is incubated with a mixture of antibodies to the drugs to be tested. During this time any drug in the sample reacts with these antibodies. If there is drug in the sample, the antibodies are bound by the sample. On the other hand, if the sample is drug-free, antibody will remain unbound. In step 2, the drug-digoxin-bis-biotin linked sensitizer beads are added to the mixture and this reagent is allowed to bind to any free anti-drug antibody. Finally, the anti-digoxin linked chemiluminescer beads are added. If the sample is positive for drug, the digoxin on the sensitizer bead is free to bind with the anti-digoxin on the chemiluminescer bead and there is signal. If the sample is drugfree, the drug on the sensitizer bead is bound to the anti-drug and the beads are blocked from interacting. The assay is a "yes or no" assay and is not quantitative.

The assay procedure employed was as follows:

Step 1

Reagent 1 consisted of a mixture of antibodies to the drugs to be measured (20 µg anti-morphine antibody+60 µg polyclonal anti-benzoylecgonine). To assay buffer (45 µl) was added 35 µl of Reagent 1. Then, 20 µl of sample was added. Reagent 1, sample and buffer were delivered together into a TECAN instrument (Tecan Instruments, Hombrecktikon, Switzerland) and the mixture was incubated at 37° C. for 144 sec.

Step 2

Reagent 2 consisted of a mixture of the decorated sensitizer beads (2.5 µg sensitizer beads decorated with morphine-digoxin-bis-biotin and 2.5 µg sensitizer beads decorated with benzoylecgonine-digoxin-bis-biotin). In step 2, to 180 µl assay buffer was added 20 µl of Reagent 2. Reagent 2 and buffer were delivered together into a TECAN and the mixture was incubated for 27.5 sec at 37° C.

Step 3

Reagent 3 consisted of chemiluminescer beads saturated with ant-digoxin (1.0 µg anti-digoxin coated acceptor beads) were then added and the entire mixture was incubated for an 20 additional sec. In step 3, 680 µl assay buffer was added, followed by 20 µl Reagent 3. Reagent 3 and buffer were delivered together into the cuvette and the mixture was incubated for 20 sec at 37° C.

Step 4

Signal was read at 10 cycles, illumination time=1.0 sec, read time=1.0 sec. The signal is expressed in relative light units (RLU). Samples and reagents were maintained on the machine at 4° C. Assay buffer was maintained at 37° C.

Standard curves were run for both drugs in this screening assay. The backgrounds for this multi-drug screening assay are additive and, therefore, twice that of each single assay; however, positive samples at the cut-off levels of each drug can be accurately measured. The readings for the screening assay are presented in Table 1, using both benzoylecgonine and morphine calibrators.

TABLE 1

Calibrator Readings for the Screening Assay

| Screening Assay Using Benzoylecgonine Calibrators | | Screening Assay Using Morphine Calibrators | |
|---|---|---|---|
| Benzoylecgonine (ng/ml) | Signal (RLU) | Morphine (ng/ml) | Signal (RLU) |
| 0 | 56927 | 0 | 56927 |
| 150 | 67104 | 500 | 60239 |
| 300 | 91327 | 2000 | 93525 |
| 750 | 119105 | 3500 | 130411 |
| 1500 | 120591 | 5000 | 140520 |
| 3000 | 123844 | 10000 | 142561 |

Twenty-one samples positive for morphine (both above and below the cut-off level) and 20 cocaine-containing samples were run in the screening assay. The results are compared with those obtained for GC/MS and presented in Tables 2 and 3. The screening assay of the invention measured as positive all samples that were above the respective cut-off levels regardless of which drug was used to make the calibrator set. In other words the present assay resulted in neither false positives nor false negatives regardless of the kind of drug in the sample.

TABLE 2

Opiate-Positive Samples In the Screening Assay

| Sample | GC/MS Morphine | GC/MS Codeine | Screening Assay Using Benzoylecgonine Calibrators** | Screening Assay Using Morphine Calibrators*** |
|---|---|---|---|---|
| 1 | 510 | | −26.1 | 51.1 |
| 2 | 696 | | 26.1 | 93.5 |
| 3 | 398 | | OR | OR |
| 4 | 7191 | 1126 | OR | OR |
| 5 | 604 | | 162.6 | 1231.4 |
| 6 | 997 | 35,020 | OR | OR |
| 7 | 1050 | 117 | 192.9 | 1401.8 |
| 8 | 1356 | | 257.2 | 1737.8 |
| 9 | 6058 | 908 | OR | OR |
| 10 | 369 | | 188.8 | 1379.8 |
| 11 | 4671 | 282 | OR | OR |
| 12 | 2289 | | OR | OR |
| 13 | 2078 | 107 | OR | 3033.0 |
| 14 | 403 | | 110.9 | 926.4 |
| 15 | 1119 | | 27.7 | 403.6 |
| 16 | 2924 | | OR | OR |
| 17 | 732 | | 172.7 | 1289.2 |
| 18 | 1678 | | 209.8 | 1493.9 |
| 19 | 1167 | | OR | OR |
| 20 | 4807 | 957 | OR | OR |
| 21 | 926 | | 29.3 | 413.7 |

*OR = Positive but Out of Range
**Samples above 300 ng/ml = Positive
***Samples above 2000 ng/ml = Positive

TABLE 3

Cocaine-Positive Samples In the Screening Assay

| Sample | GC/MS Opiates | GC/MS Benzoylecgonine | LOCI Using Benzoylecgonine Calibrators** | LOCI Using Morphine Calibrators*** |
|---|---|---|---|---|
| 1 | >1000 | >1000 | OR | OR |
| 2 | | >1000 | 721 | 2820 |
| 3 | | >1000 | 400 | 2294 |
| 4 | | >1000 | OR | 3189 |

TABLE 3-continued

Cocaine-Positive Samples In the Screening Assay

| Sample | GC/MS Opiates | GC/MS Benzoylecgonine | LOCI Using Benzoylecgonine Calibrators** | LOCI Using Morphine Calibrators*** |
|---|---|---|---|---|
| 5  |       | >1000 | OR | OR |
| 6  |       | >1000 | OR | OR |
| 7  |       | 726   | OR | OR |
| 8  |       | >1000 | OR | OR |
| 9  |       | >1000 | OR | OR |
| 10 |       | >1000 | OR | OR |
| 11 |       | 875   | OR | 4126 |
| 12 |       | 677   | OR | OR |
| 13 |       | 523   | OR | 3158 |
| 14 |       | >1000 | OR | OR |
| 15 |       | >1000 | OR | OR |
| 16 |       | 314   | OR | 3093 |
| 17 | >1000 | >1000 | OR | 4692 |
| 18 |       | 732   | OR | 4588 |
| 19 |       | 538   | OR | 3464 |
| 20 | >1000 | >1000 | OR | OR |

*OR = Positive but Out of Range
**Samples above 300 ng/ml = Positive
***Samples above 2000 ng/ml = Positive The above results demonstrate that a screening assay in accordance with the present invention for morphine combined with cocaine gives accurate, reliable results.

The above discussion includes certain theories as to mechanisms involved in the present invention. These theories should not be construed to limit the present invention in any way, since it has been demonstrated that the present invention achieves the results described.

Although the foregoing invention has been described in some detail by way of illustration and example for purposes of clarity and understanding, it will be obvious that certain changes or modifications may be practiced within the scope of the appended claims.

What is claimed is:

1. A method for determining the presence of one or more drugs in a sample suspected of containing any of a plurality of said drugs, said method comprising:
   (a) combining in a medium said sample and an antibody for each of said drugs,
   (b) adding to said combination, for each of said drugs, a first reagent that is a conjugate comprising (i) a first label, (ii) a small molecule and (iii) a drug analog, wherein said drug analog competes with said drug, if present, for binding to said antibody for said drug,
   (c) adding to said combination a second reagent that is a conjugate comprising (i) a second label and (ii) an antibody for said small molecule, wherein said first label and said second label interact in close proximity to produce a predetermined increased amount of signal if one or more of said drugs are present in said sample, wherein said antibody for said drug binds to said drug analog of said first reagent thereby inhibiting the binding of said antibody for said molecule to said small molecule,
   (d) examining said medium for the amount of said signal, said predetermined increased amount thereof being related to the presence of one or more of said drugs in said sample.

2. A method according to claim 1 wherein said small molecule is selected from the group consisting of drugs, biotin and dyes.

3. A method according to claim 1 wherein said first reagent is bound to a particle.

4. A method according to claim 1 wherein said second reagent is bound to a particle.

5. A method according to claim 1 wherein said first and second labels are selected from the group consisting of a luminescent energy donor and acceptor pair, a singlet oxygen generator and chemiluminescent reactant pair, and an enzyme pair wherein a product of the first enzyme serves as a substrate for the second enzyme.

6. A method according to claim 1 wherein one of said first label or said second label is an enzyme and the other of said labels is an enzyme that is different from the first enzyme and a product of the reaction of the enzyme comprising the first label is a substrate for the other of said enzymes.

7. A method according to claim 1 wherein one of said first label or said second label is a chemiluminescent compound and the other of said labels is a sensitizer.

8. A method according to claim 1 wherein one of said first label or said second label is an energy donor or acceptor and the other of said labels is a fluorescent compound.

9. A kit for determining the presence of one or more drugs in a sample suspected of containing any of a plurality of said drugs, said kit comprising in packaged combination:
   (a) an antibody for each of said drugs,
   (b) for each of said drugs, a first reagent that is a conjugate comprising a first label, a small molecule and a drug analog, and
   (c) a second reagent that is a conjugate comprising a second label and an antibody for said small molecule, wherein said first label and said second label are capable of interacting in close proximity to modulate a signal if one or more of said plurality of drugs are present in said sample.

10. A kit according to claim 9 wherein said small molecule is selected from the group consisting of drugs, biotin and dyes.

11. A kit according to claim 9 wherein said first reagent is bound to a particle.

12. A kit according to claim 9 wherein said second reagent is bound to a particle.

13. A kit according to claim 9 wherein said first and second labels are selected from the group consisting of a luminescent energy donor and acceptor pair, a singlet oxygen generator and chemiluminescent reactant pair, and an enzyme pair wherein a product of the first enzyme serves as a substrate for the second enzyme.

14. A kit according to claim 9 wherein one of said first label or said second label is an enzyme and the other of said labels is an enzyme that is different from the first enzyme and the product of the reaction of the enzyme comprising the first label is a substrate for the other of said enzymes.

15. A kit according to claim 9 wherein one of said first label or said second label is a chemiluminescent compound and the other of said labels is a sensitizer.

16. A kit according to claim 9 wherein one of said first label or said second label is an energy donor or acceptor and the other of said labels is a fluorescent compound.

* * * * *